United States Patent [19]

Tan et al.

[11] Patent Number: 5,037,977
[45] Date of Patent: Aug. 6, 1991

[54] METHOD FOR PRODUCTION OF DIMERIC ALKALOIDS

[75] Inventors: Hiroaki Tan; Naoya Sakamoto; Eiichiro Hata; Takeshi Ishitoku; Noriaki Kihara, all of Yamaguchi, Japan

[73] Assignee: Mitsui Petrochemical Industries Ltd., Tokyo, Japan

[21] Appl. No.: 390,903

[22] Filed: Aug. 8, 1989

[30] Foreign Application Priority Data

Aug. 11, 1988 [JP] Japan .............................. 63-198897
Aug. 11, 1988 [JP] Japan .............................. 63-198898

[51] Int. Cl.$^5$ .......................................... C07D 519/04
[52] U.S. Cl. ...................................... 540/478; 546/51
[58] Field of Search ........................................ 540/478

[56] References Cited

U.S. PATENT DOCUMENTS 4,279,817  7/1981  Kutney ................................ 540/478
4,737,586  4/1988  Potier et al. ........................ 540/478
4,778,885 10/1988  Vukovic et al. ..................... 540/478

FOREIGN PATENT DOCUMENTS 3801450  8/1988  Fed. Rep. of Germany ...... 540/478
2544319 10/1984  France ............................... 540/478

Primary Examiner—Diana Rivers
Attorney, Agent, or Firm—Nixon & Vanderhye

[57] ABSTRACT

This invention concerns a method for the production of dimeric alkaloids, characterized by reacting of catharanthine with vindoline in the presence of $Fe^{3+}$ and (1) removing or inactivating the $Fe^{3+}$ and allowing the reaction product to react with a reducing agent or (2) allowing presence of oxygen and a dicarboxylic acid or a derivative thereof in the reaction system and allowing the reaction product to react with a hydride source.

In accordance with this invention, such dimeric alkaloid as vinblastine, leurosidin, and 3′,4′-anhydrovinblastine which are useful as antineoplastic drugs can be produced in high yields.

4 Claims, No Drawings

METHOD FOR PRODUCTION OF DIMERIC ALKALOIDS

BACKGROUND OF THE INVENTION

1. Field of the Invention

This invention relates to an improved method for producing in high yields such dimeric alkaloids as vinblastine leurosidene, and 3',4'-anhydrovinblastine which are useful as antineoplastic drugs.

More specifically, this invention relates to a method for the production of a dimeric alkaloid, characterized by a procedure which comprises causing reaction of catharanthine with vindoline in the presence of $Fe^{3+}$, then (1) removing or inactivating the $Fe^{3+}$ and allowing a reducing agent to react on the resultant compound or (2) allowing the presence of oxygen and a dicarboxylic acid or a derivative thereof in the reaction system and then causing the resultant compound to react with a hydride source.

2. Description of the Prior Art

Such dimeric alkaloids as vinblastine and 3',4'-anhydrovinblastine have been known in the art as compounds possessing an antineoplastic activity (U.S. Pat. No. 4,029,663). As means of obtaining these compounds, methods which consist in extracting the compounds from a plant of genus Catharanthus, having the scientific name of Catharanthus roseous (alias Vinca rosea), and methods which resort to chemical synthesis using catharanthine and vindoline derived from the plant as starting materials have been known to the art.

The methods by extraction, however, entail difficulties in separation and purification of the dimeric alkaloids because the plant has a very small dimeric alkaloids content and also because a number of analogous compounds are additionally present in the plant.

Among the methods resorting to chemical synthesis, the method which comprises oxidizing catharanthine with a peracid, acylating the resultant N-oxide, causing reaction of the acylated product with vindoline and reducing the reaction product with NaBH$_4$ (U.S. Pat. No. 4,144,237) has been known to the art.

The synthesis mentioned above, however, attains isolation of 3',4'-anhydrovinblastine only in a low yield of 41% and simultaneously gives rise to 10% of isomers as a by-product. Thus, this method entails difficulties in separation and purification of the dimeric alkaloids.

SUMMARY OF THE INVENTION

The inventors, mindful of commercialized production of the dimeric alkaloids, have found a special interest in the method which comprises effecting coupling of catharanthine with vindoline in the presence of $Fe^{3+}$ and then causing the product of coupling to react with a reducing agent or a hydride source. They have tried the reaction of the product of coupling with various reducing agents or hydride sources, to find that this method is not particularly effective in improving the yield of the dimeric alkaloids.

The inventors have continued a study with a view to improving the yield of the dimeric alkaloids, to acquire an unexpected and useful novel knowledge that by (1) removing or inactivating the $Fe^{3+}$ or (2) allowing the presence of oxygen and a dicarboxylic acid or a derivative thereof in the reaction system after the coupling reaction and prior to the addition of the reducing agent or the hydride source, the yield of 3',4'-anhydrovinblastine is notably improved in the former case (1) or the yield of vinblastine which has found actual utility as a cancer depressant is greatly improved in the latter case (2).

DETAILED DESCRIPTION OF THE INVENTION

This invention embraces the following methods as aspects thereof.

(1) A method for the production of a dimeric alkaloid, characterized by a procedure which comprises causing reaction of catharanthine with vindoline in the presence of $Fe^{3+}$ and then (1) removing or inactivating the $Fe^{3+}$ and allowing a reducing agent to react on the reaction product or (2) allowing presence of oxygen and a dicarboxylic acid or a derivative thereof in the reaction system and then causing the reaction product to react with a hydride source.

(2) A method for the production of 3',4'-anhydrovinblastine, characterized by a procedure which comprises causing reaction of catharanthine with vindoline in the presence of $Fe^{3+}$ and then removing or inactivating the $Fe^{3+}$ and subsequently reducing the reaction product.

(3) A method for the production of 3',4'-anhydrovinblastine set forth in (2) above, characterized by effecting the inactivation of the $Fe^{3+}$ by the addition of an iron ligand.

(4) A method for the production of a dimeric alkaloid, characterized by a procedure which comprises causing reaction of catharanthine with vindoline in the presence of $Fe^{3+}$, then allowing presence of oxygen and a dicarboxylic acid or a derivative thereof in the reaction system, and causing the reaction product to react with a hydride source.

(5) A method for the production of a dimeric alkaloid set forth in (4) above, characterized by the fact that the dicarboxylic acid is oxalic acid, malonic acid, or a 2-position substituted malonic acid and the dimeric alkaloid is a compound selected from the group consisting of vinblastine, leurosidine, and 3',4'-anhydrovinblastine.

In the working of this invention, the reaction of catharanthine with vindoline in the presence of $Fe^{3+}$ can be carried out as conventionally practiced. Generally this reaction brings about desirable results when it is carried out in an atmosphere of nitrogen or under a current of nitrogen.

Now, the method which comprises the steps of removing or inactivating $Fe^{3+}$ after the coupling reaction and causing reaction of the product of coupling reaction with a reducing agent will be described in detail below.

The removal of $Fe^{3+}$ is attained by adding a basic compound to the reaction mixture after completion of the coupling reaction thereby inducing precipitation of $Fe^{3+}$ and removing the precipitate from the reaction system by such a conventional solid-liquid separation technique as filtration or centrifugal separation. The basic compound to be used herein may be any of the basic compounds which are capable of inducing the precipitation of $Fe^{3+}$ without impeding the reaction. The basic compounds which may be mentioned include metal hydroxides such as sodium hydroxide, potassium hydroxide, calcium hydroxide, and barium hydroxide; carbonates such as potassium carbonate, sodium carbonate and ammonium carbonate; bicarbonates such as sodium bicarbonate and potassium bicarbonate; amines such as urea, methylamine, ethylamine, dimethylamine, and trimethylamine; hydroxides of quarternary ammonium such as tetraethyl ammonium hydroxide and aqueous ammonia.

The term "inactivation of $Fe^{3+}$" refers to any treatment which is capable of eliminating or blocking the adverse effects or impeditive actions of $Fe^{3+}$ otherwise manifested in the subsequent steps.

The treatment for the inactivation of $Fe^{3+}$, therefore, extensively embraces treatments capable of inhibiting the coordination of iron to useful components in the subsequent steps and actions capable of inhibiting the oxidation by iron. For example, a method which comprises adding an iron ligand to the reaction system after completion of the coupling reaction thereby inactivating the $Fe^{3+}$ for the purpose of precluding the adverse effects or impeditive actions of $Fe^{3+}$, a method which effects inactivation by reducing the $Fe^{3+}$ to metallic iron or to $Fe^{2+}$, and a method which comprises producing different species of ligand by the action of different species of ligands and causing the resultant complexes to be coprecipitated as complex salts or converted into nontoxic solubles are included. Further, a method which either allows the precipitate of $Fe^{3+}$ with the basic compound to remain wholly in the reaction system or removing part of the precipitate and allowing the remainder thereof to remain in the reaction system constitutes itself one of preferred measures for attaining the inactivation.

The method for inactivating $Fe^{3+}$ by the addition of an iron is a method which comprises adding a compound capable of being coordinated to the iron, i.e. $Fe^{3+}$. Though the following compounds may be cited as examples of the iron ligands which are usable in the present invention, a wide variety of other complexing agents are similarly usable.

Lower fatty acids: Formic acid, acetic acid, propionic acid, butyric acid, valeric acid, trimethyl acetic acid, caproic acid, enanthic acid, and caprylic acid.

Dicarboxylic acids: Aliphatic dicarboxylic acids (oxalic acid, malonic acid, succinic acid, glutaric acid, adipic acid, maleic acid, fumaric acid, and pimelic acid) and aromatic dicarboxylic acids (phthalic acid, isophtalic acid, and terephthalic acid).

Ketocarboxylic acids: pyruvic acid.

Hydroxycarboxylic acids: Aliphatic hydroxycarboxylic acids (glycolic acid, lactic acid, hydroxyacrylic acid, glyceric acid, malic acid, tartaric acid, succinic acid, and citric acid) and aromatic oxycarboxylic acids (salicylic acid, oxybenzoic acid, and gallic acid).

Diols: Ethylene glycol, catechol and ascorbic acid.

Polyaminocarboxylic acids: EDTA.

Sugar derivatives: Glucose, fructose, sucrose, and arbutin.

Salts of the foregoing compounds.

Cyanides: Potassium cyanide, sodium cyanide, and tributyl ammonium cyanide.

Thiocyanides: Potassium thiocyanide, sodium thiocyanide, and tributyl ammonium thiocyanide.

Fluorides: Sodium fluoride and potassium fluoride.

Pyridine derivatives: Phenanthrene derivatives and bipyridine derivatives.

Phosphoric acids and condensed phosphoric acids: Polyphosphoric acid, methaphosphoric acid, pyrophosphoric acid, phosphoric acid and salts thereof.

Such an iron ligand is desired to be added in an amount in the range of 0.5 to 200 mol, preferably 1 to 10 mol, per mol of $Fe^{3+}$.

After the inactivation of $Fe^{3+}$ is carried out as described above, a reducing agent is added to the reaction system to give the compound aimed at.

When the precipitate of $Fe^{3+}$ is produced by the treatment of inactivation, the treatment mentioned above may be performed on the reaction liquid such as the filtrate which remains after the removal of the precipitate. The precipitate which is removed from the reaction system is washed with an organic solvent. The washings are combined with the reaction liquid such as the filtrate or the supernatant, concentrated under a vacuum to expel the organic solvent, admixed with water, and then reduced with a reducing agent such as $NaBH_4$. Otherwise, the mixture of the washings with the reaction liquid, without being concentrated under a vacuum, may be adjusted to a pH value of less than 6, subjected to solid-liquid separation, with the water layer reduced by the addition of a reducing agent such as $NaBH_4$. The precipitate produced in consequence of the treatment of inactivation is not necessarily removed from the reaction system. When the treatment of inactivation is carried out in a liquid state, the reaction mixture is subjected to extraction of the water layer with an organic solvent. The organic layer consequently obtained is concentrated under a vacuum, admixed with water, and then reduced.

As examples of the reducing agents which are usable herein, the following compounds may be cited unexclusively.

Hydrides: Sodium borohydride, potassium borohydride, lithium borohydride, and sodium cyanoborohydride.

Metals: Zinc, iron, tin, alumimum, and magnesium.

When such a reducing agent as mentioned above exhibits an excessively high reducing power, the excessive reducing power may be suitably adjusted by decreasing the amount of the reducing agent to be used or having the reducing agent itself suitably modified or masked.

Though the coupling reaction may be performed in an atmosphere of air, it brings about better results when it is carried out in an atmosphere of nitrogen or under a current of nitrogen.

The 3',4'-anhydrovinblastine which is formed by the method described above can be isolated by extraction with an organic solvent.

By this method, since the compound aimed at is obtained in a very high purity, it can easily be crystallized. Thus, it can be thoroughly recovered by recrystallization without requiring any of the preliminary treatments for isolation and purification by the use of a column which have been an indispensable requirement for the conventional method. Since the separation of the product is easy as described above, the present method is highly suitable for commercial production.

Now, the method which comprises the steps of allowing presence of oxygen and a dicarboxylic acid or a derivative thereof in the reaction system after the coupling reaction and causing the product of the coupling reaction to react with a hydride source will be described in detail below.

This method starts with causing reaction of catharantine with vindoline in the presence of $Fe^{3+}$. Desirably, this reaction is carried out in an atmosphere of nitrogen or under a current of nitrogen until the addition of a dicarboxylate. After the addition of the dicarboxylate, the reaction is desired to be continued in an atmosphere of air, under a current of air, in an atmosphere of oxygen, or under a current of oxygen.

The addition of the dicarboxylate is then followed by the addition of a hydride source. The hydride sources which are usable in this method include sodium borohydride, potassium borohydride, sodium cyanoborohydride, amine complexes of borane, for example. Desirably, such a hydride source is added in an amount in the range of 0.05 to 10 mol, preferably 0.1 to 1 mol, per mol of $Fe^{3+}$.

The dicarboxylic acids which are usable herein include aliphatic dicarboxylic acids, alicyclic dicarboxylic acids, aromatic dicarboxylic acids, and heterocyclic dicarboxylic acids, for example. They may be used either singly or in a freely combined form. In this invention, these dicarboxylic acids can be extensively used without reference to discrimination between saturation and unsaturation. As concrete examples of these dicarboxylic acids, oxalic acid, malonic acid, succinic acid, glutaric acid, adipic acid, pimelic acid, maleic acid, fumaric acid, phthalic acid, isophthalic acid, terephthalic acid, and the derivatives of such acids may be unexclusively cited. Among other dicarboxylic acids mentioned above, saturated aliphatic dicarboxylic acids are usable particularly advantageously. The saturated aliphatic dicarboxylic acids which are fit for use herein include oxalic acid and malonic acid and such 2-positionsubstituted malonic acids as 2-hydroxymalonic acid, 2-methylmalonic acid, 2-ethylmalonic acid, 2,2-dimethylmalonic acid, 2-aminomalonic acid, 2-nitromalonic acid, 2,2-dihydroxymalonic acid, 2-phenylmalonic acid, and 2-benzylmalonic acid, for example.

Besides the free acids mentioned above, salts, amides, and other similar derivatives of such acids are similarly usable for the present reaction. The bases which are usable for the formation of such salts include such alkali metals as sodium, potassium, and lithium and amines such as ammonia, methylamine, dimethylamine, trimethylamine, and ethylamine, for example. Such quarternary ammonium salts as tetramethyl ammonium, tetraethyl ammonium, tetrapropyl ammonium, tetrabutyl ammonium, and trimethylbenzyl ammonium are similarly usable. Ammonium oxalate, methyl ammonium oxalate, potassium oxalate, ammonium malonate, and potassium malonate are preferably usable on account of desirable form of salt.

The salt of a dicarboxylic acid to be added is desired to be used in an amount in the range of 1 to 10 mol, preferably 1 to 4 mol, per mols of $Fe^{3+}$.

The solvents which are usable in this reaction include ketones such as acetone and methylethyl ketone, tetrahydrofuran alcohols such as methanol, and ethanol, acetonitrile, DMF, DMSO, and water, for example. Optionally, a mixture of such solvents may be used. Desirably, water alone or a mixed solvent of water and methanol may be used. The reaction can be carried out at a temperature between the level above the melting point of the reaction solvent and 50° C. Desirably, this reaction temperature is in the range of −10° to 10° C.

The dimeric alkaloid which is formed by this reaction can be obtained by basifying the reaction system containing the product by treatment with the hydroxide of an alkali metal, a (bi)carbonate, urea, ammonia, or an amine and then extracting the dimeric alkaloid with an organic solvent.

Since this method produces various species of dimers, such dimers may be separated from one another. These dimers in the mixed state manifest an antineoplastic activity and therefor, they may be utilized in the mixed state. In this case, they can be expected to manifest various physiological activities other than the antineoplastic activity. By this method, dimeric alkaloids such as leurosidine and 3',4'-anhydrovinblastine are formed in increased yields and vinblastine is formed in a remarkable high yield.

Now, the present invention will be described more specifically below with reference to working examples.

EXAMPLE 1

In a reaction vessel having an inner volume of 500 ml, 180 ml of water was placed, swept with $N_2$ gas and, at the same time, cooled with ice. To this water, a solution of 184 mg (480 μmol) of a half-sulfate of catharanthine in 20 ml of water and a solution of 220 mg (480 μmols) of vindoline in 20 ml of water and 0.4 ml of 2N-HCl were added. To the resultant mixture, a solution of 8.1 g of $FeCl_3.6H_2O$ in 50 ml of water was added to induce reaction. Under a continuous forced introduction of $N_2$, the reaction mixture was stirred for three hours under ice-cooling ice and a solution of 12.2 g of NaOAc in 50 ml of water was added. The resultant mixture and 227 mg of $NaBH_4$ added in a solid state thereto were stirred for 30 minutes. The reaction mixture was extracted four times with 100 ml of ethyl acetate. The organic layer consequently separated was dried over anhydrous sodium sulfate and then concentrated under a vacuum. The residue of the concentration was dissolved in 30 ml of chloroform and then washed with 50 ml of a saturated aqueous solution of $NaHCO_3$. The organic layer dried over anhydrous sodium sulfate and then concentrated. The residue of concentration, on mixing with 2 ml of methanol, precipitated crystals. When the crystals were separated by filtration, there were obtained 304 mg of colorless crystals of 3',4'-anhydrovinblastine having a melting point of 200° C. (decomposition). The yield of the product was 80%. This compound gave signals at 3.89 (3H, S) and 3.54 (3H S) in the $^1$H-nmr(CDCl$_3$). Thus, they were identified as natural 3',4'-anhydrovinblastine.

EXAMPLE 2

In a reaction vessel having an inner volume of 50 ml, 10 ml of water was placed, kept cooled with ice and, at the same time, bubbled with nitrogen for 30 minutes. To this water, 200 μl (2.39 μmol) of an aqueous 11.9 mM catharanthine half-sulfate solution, 200 μl (2.41 μmol) of 12.0 mM vindoline hydrochloride solution, and 1.0 ml (1.20 m mols) of an aqueous 1.2M ferric chloride solution were added sequentially in the order mentioned. The mixture was kept cooled with ice and bubbled with nitrogen and, at the same time, stirred for three hours. The mixture was alkalinized by addition of 1 ml of 25% aqueous ammonia and extracted three times with 10 ml of ethyl acetate. The extract consequently collected was dried up under a vacuum, dissolved in 10 ml of water and 24 μl of 2N-HCl, and then stirred in conjunction with 1 ml of an aqueous 227 mM NaBH4 solution for 30 minutes. Then, the reaction mixture was admixed with 2 ml of 25% aqueous ammonia and extracted three times with 10 ml of ethyl acetate.

The extract collected was dried up under a vacuum at a temperature of not higher than 40° C. and then analyzed by HPLC under the following conditions. Consequently, 3',4'-anhydrovinblastine was obtained in a yield of 89%.

Column: YMC-packed column, AM-312 (S-5 120A ODS).
Solvent: A 3:2 mixture of $CH_3CN$ and an aqueous 0.01M ammonium carbonate solution.
Flow rate: 1 ml/min.
Column temperature: 45° C.
Detection wavelength: 254 nm
Retention time: 3',4'-Anhydrovinblastine (40.8 minutes)

EXAMPLE 3

3',4'-Anhydrovinblastine was obtained in a yield of 88% by following the procedure of Example 2, except for 634 mg (3.6 m mol) of L-ascorbic acid was added in place of 1 ml of 25% aqueous ammonia and the resultant mixture and 1 ml (227 μmols) of an aqueous 227 mM NaBH4 added thereto were stirred for 30 minutes.

EXAMPLE 4

3',4'-Anhydrovinblastine was obtained in a yield of 87% by following the procedure of Example 3, except for triammonium citrate was added in the place of L-ascorbic acid.

EXAMPLE 5

3',4'-Anhydrovinblastine was obtained in a yield of 85% by following the procedure of Example 3, except for sodium pyruvate was added in place of L-ascorbic acid.

EXAMPLE 6

3',4'-Anhydrovinblastine was obtained in a yield of 87% by following the procedure of Example 3, except for oxalic acid was added in place of L-ascorbic acid.

EXAMPLE 7

3',4'-Anhydrovinblastine was obtained in a yield of 88% by following the procedure of Example 3, except for malic acid was added in place of L-ascorbic acid.

EXAMPLE 8

3',4'-Anhydrovinblastine was obtained in a yield of 84% by following the procedure of Example 3, except for maleic acid was added in place of L-ascorbic acid.

EXAMPLE 9

3',4'-Anhydrovinblastine was obtained in a yield of 85% by following the procedure of Example 3, except for sodium fluoride was added in place of L-ascorbic acid.

EXAMPLE 10

3',4'-Anhydrovinblastine was obtained in a yield of 82% by following the procedure of Example 3, except for arbutin was added in place of L-ascorbic acid.

EXAMPLE 11

In a reaction vessel having an inner volume of 50 ml, 10 ml of water was placed, kept cooled with ice and, at the same time, bubbled with nitrogen for 30 minutes. To this water, 200 μl (2.39 μmol) of an aqueous 11.9 mM catharanthine half-sulfate, 200 μl (2.41 μmols) 12.0 mM vindoline hydrochloric solution, and 1.0 ml (1.20 m mol) of an aqueous 1.2M ferric chloride solution were added sequentially in the order mentioned. The resultant mixture was kept cooled with ice and bubbled with nitrogen and, at the same time, stirred for three hours. Then, the resultant mixture and 0.51 g (3.6 m mol) of ammonium oxalate added thereto were bubbled with air and kept cooled with ice and, at the same time, stirred for 30 minutes. After 30 minutes following the completion of the stirring, the resultant reaction mixture was stirred in conjunction with 1 ml 227 μmol) of an aqueous 227 mM NaBH4 solution for 30 minutes Thereafter, the resultant reaction mixture was alkalinized by addition of 2.00 ml of 25% aqueous ammonia and extracted three times with 10 ml each of ethyl acetate.

The extract consequently collected was dried up under a vacuum at a temperature of not higher than 40° C. and analyzed by HPLC under the following conditions. As the result, vinblastine and leurosidine were obtained in respective yields of 30% and 11%.

Column: YMC-packed column, Am-312 (S-5 120A ODS).
Solvent: A 3:2 mixture of $CH_3CN$: Aqueous 0.01M ammonium carbonate solution
Flow rate: 1 ml/min.
Column temperature: 45° C.
Detection wavelength: 254 nm
Retention time: Leurocidin (10.8 to 15 minutes: variable with the time of use of the column), vinblastine (12.5 minutes), and 3+,4'-anhydrovinblastine (40.8 minutes)

EXAMPLE 12

Vinblastine and leurosidin were obtained in the respective yields of 27% and 12% by following the procedure of Example 11, except for ammonium malonate was added in place of ammonium oxalate.

EXAMPLE 13

Vinblastine and leurosidin were obtained in the respective yields of 32% and 11% by following the procedure of Example 11, except for methyl ammonium oxalate was added in place of ammonium oxalate.

EXAMPLE 14

Vinblastine and leurosidin were obtained in the respective yields of 28% and 19% by following the procedure of Example 11, except for tetramethyl ammonium oxalate was added in place of ammonium oxalate.

EXAMPLE 15

Vinblastine and leurosidin were obtained in the respective yields of 28% and 20% by following the procedure of Example 11, except for potassium oxalate was added in place of ammonium oxalate.

EXAMPLE 16

Vinblastine and leurosidin were obtained in the respective yields of 27% and 14% by following the procedure of Example 11, except for ammonium 2-methylmalonate was added in place of ammonium oxalate.

As demonstrated in Examples 1 to 10, this invention allows 3',4'-anhydrovinblastine to be produced in a yield of 89% as compared with the conventional yield of 68.6% and further allows this product to be produced in the form of highly pure crystals of without requiring separation or purification. Further as demonstrated in Examples 11 to 16, this invention allows an improvement of more than 10% in the yields of vinblastine as compared with the conventional method which contemplates no addition of any dicarboxylate to the reaction system. In the light of very high price of vinblastine as a medicine, this improvement in yields promises a great economic contribution.

What is claimed is:

1. A method for producing a dimeric alkaloid which comprises
   (a) reacting catharanthine with vindoline in the presence of $Fe^{3+}$ to form a reaction product,
   (b) adding an iron ligand to inactivate the $Fe^{3+}$, and thereafter
   (c) reducing the reaction product with a reducing agent.

2. The method according to claim 1 wherein said dimeric alkaloid is selected from the group consisting of vinblastine, leurosidine, and 3',4'-anhydrovinblastine.

3. A method for producing a dimeric alkaloid which comprises:
   (a) reacting catharanthine with vindoline in the presence of $Fe^{3+}$ and also in the presence of oxygen and a dicarboxylic acid or a derivative thereof, and thereafter
   (b) reacting the reaction product of step (a) with a hydride source.

4. The method according to claim 3, wherein said dicarboxylic acid is oxalic acid, malonic acid, or a 2-position substituted malonic acid and said dimeric alkaloid is a compound selected from the group consisting of vinblastine, leurosidin, and 3',4'-anhydrovinblastine.

* * * * *